United States Patent [19]

Oyama et al.

[11] Patent Number: 4,594,450
[45] Date of Patent: Jun. 10, 1986

[54] PROCESS FOR PRODUCING AN α-HALOGENO-β-PHENYLPROPIONIC ACID

[75] Inventors: Kiyotaka Oyama, Hikari; Tuneo Harada, Shin-nanyo, both of Japan

[73] Assignee: Toyo Soda Manufacturing Co., Ltd., Shin-nanyo, Japan

[21] Appl. No.: 660,369

[22] Filed: Oct. 12, 1984

[51] Int. Cl.⁴ .............................. C07C 57/30
[52] U.S. Cl. .................................. 562/496
[58] Field of Search ........................ 562/496

[56] References Cited
FOREIGN PATENT DOCUMENTS
6158732  7/1981  Japan ................... 562/496

OTHER PUBLICATION
Chemical Abstract, Vol 52, No. 11, Jun. 10, 1958, Column 9091 i–90206.

*Primary Examiner*—Paul J. Killos
*Attorney, Agent, or Firm*—Oblon, Fisher, Spivak, McClelland & Maier

[57] ABSTRACT

A process for producing an α-halogeno-β-phenylpropionic acid represented by the general formula:

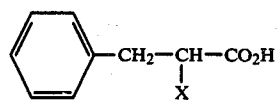

(I)

where X is a halogen atom, which comprises hydrolyzing under heating a halogen-containing ethylbenzene derivative represented by the general formula:

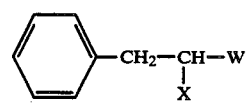

(II)

where W is a cyano group, an amidocarbonyl group or a lower alkoxycarbonyl group, and X is as defined above, in an aqueous mineral acid solution under vigorous stirring.

7 Claims, No Drawings

PROCESS FOR PRODUCING AN α-HALOGENO-β-PHENYLPROPIONIC ACID

The present invention relates to a process for preparing an α-halogeno-β-phenylpropionic acid. More particularly, the present invention relates to a process for producing an α-halogeno-β-phenylpropionic acid by hydrolyzing a halogen-containing ethylbenzene derivative such as an α-halogeno-β-phenylpropionitrile.

An α-halogeno-β-phenylpropionic acid can readily be converted to phenylalanine by amination with e.g. ammonia, and thus very useful as an intermediate for the production of phenylalanine.

As a method for preparing an α-halogeno-β-phenylpropionic acid, it is known to react α-chloro-β-phenylpropionitrile with 85% formic acid and concentrated hydrochloric acid (A. V. Dombrovskii et al.; Chemical Abstract, vol. 52, 9019i (1958)). However, in this method, the reaction is conducted under a severe condition i.e. reflux, for a long period of time i.e. as long as 10 hours.

On the other hand, an improved method has been proposed wherein the hydrolysis is conducted in a short period of time by heating in the presence of a mineral acid and acetic acid or propionic acid (Japanese Unexamined Patent Publication No. 158732/1981).

In these methods, it is necessary to recover the organic acid used as the solvent, from the reaction mixture after the completion of the reaction. However, when the organic acid is recovered by distillation from the reaction mixture, crystals of the α-halogeno-β-phenylpropionic acid precipitate, and if concentrated too much, it becomes difficult to transport these crystals to the subsequent step. For this reason, it becomes difficult to recover the organic acid quantitatively, thus leading to a loss of the organic acid.

The present inventors have conducted extensive researches for industrially advantageous hydrolysis of an α-halogeno-β-phenylpropionitrile, etc., and surprisingly found that this reaction which has been believed to hardly proceed in a reaction system other than a uniform liquid phase using an organic acid as the solvent, can efficiently proceed even in a two phase system comprising an aqueous mineral acid solution and an α-halogeno-β-phenylpropionitrile or the like, provided sufficient stirring is conducted. The present invention is based on this discovery.

Namely, the present invention provides a process for producing an α-halogeno-β-phenylpropionic acid represented by the general formula:

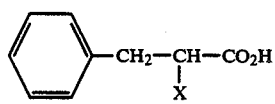
(I)

where X is a halogen atom, which comprises hydrolyzing under heating a halogen-containing ethylbenzene derivative represented by the general formula:

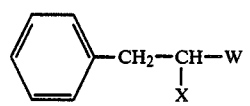
(II)

where W is a cyano group, an amidocarbonyl group or a lower alkoxycarbonyl group, and X is as defined above, in an aqueous mineral acid solution under vigorous stirring.

Now, the present invention will be described in detail with reference to the preferred embodiments.

The halogen-containing ethylbenzene derivative used as the starting material for the process of the present invention includes an α-halogeno-β-phenylpropionitrile and an amide and a lower alkyl ester of an α-halogeno-β-phenylpropionic acid. As the lower alkoxy group in the case of the lower alkyl ester, there may be mentioned a methoxy group, an ethoxy group, a propoxy group and a butoxy group. As the halogen, there may be mentioned chlorine, bromine and iodine. These compounds can readily be produced, for instance, by reacting a benzene-diazonium salt prepared from aniline, with acrylonitrile, acrylamide or an acrylate and halogen ions in the presence of a copper compound.

In the process of the present invention, as the mineral acid, there may be employed hydrochloric acid, sulfuric acid or hydrobromic acid. The amount of the mineral acid is at least about 1 mol, preferably at least about 3 mols, relative to 1 mol of the halogen-containing ethylbenzene derivative as the starting material. Further, in the reaction system, water is required to be present in an amount of at least the stoichiometric amount for the reaction. This amount is preferably at least about two times the stoichiometric amount. If the concentration of the mineral acid in the aqueous mineral acid solution is too low, the reaction rate tends to be slow, and the concentration is usually at least about 10% by weight, preferably at least about 15% by weight, more preferably at least about 20% by weight.

If the reaction temperature is low, the reaction hardly proceeds. Accordingly, the reaction temperature is preferably at least about 50° C., more preferably at least about 80° C. The upper limit is not critical, but the reaction is usually conducted below 200° C.

In the process of the present invention, no solvent is used, and the reaction is conducted in a two phase system comprising the starting material and the aqueous mineral acid solution. The reaction rate depends upon the mixing and contacting state of the two phases. In order to increase the oppotunities of the contact between the two phases, it is necessary to conduct the stirring adequately vigorously. This stirring is preferably sufficiently vigorous to maintain the reaction system in the state of an emulsion of the halogen-containing ethylbenzene and the aqueous mineral acid solution.

The reaction time may vary depending upon the reaction temperature, the amount of the mineral acid and the stirring rate. However, the reaction time is usually from about 30 to about 10 hours. After the completion of the reaction, the formed α-halogeno-β-phenylpropionic acid forms a two-phase system with the aqueous mineral acid solution phase. By separating the two phases from each other, the α-halogeno-β-phenylpropionic acid can readily be obtained.

According to the present invention, the reaction can be conducted without using any organic acid. Accordingly, the step of recovering an organic acid can be omitted, or no loss of the organic acid is involved. Further, the process of the present invention has additional advantage that after the completion of the reaction, the α-halogeno-β-phenylpropionic acid can readily be obtained.

Now, the present invention will be described in further detail with reference to Examples. However, it should be understood that the present invention is by no means restricted by these specific Examples.

EXAMPLE 1

8.28 g (50 mmol) of α-chloro-β-phenylpropionitrile was mixed with 25 ml of concentrated hydrochloric acid. The mixture was stirred at 100° C. and reacted for 2 hours while maintaining the reaction system in an emulsion state under stirring. After the completion of the reaction, the reaction mixture was cooled. The aqueous phase and the organic phase were washed twice with 20 ml of a saturated sodium chloride aqueous solution, and then left in a refrigerator overnight whereupon crystals precipitated. The crystals were dried and then weighed. The crystals (8.8 g) were confirmed to be α-chloro-βphenylpropionic acid by IR and NMR. (Yield: 95%). The crystals were recrystallized from n-hexane, whereby 8.1 g (yield: 88%) of white crystals were obtained. The melting point and the elemental analytical values of the crystals were as follows.

Melting point: 49°–51° C.
Elemental analysis: As $C_9H_9ClO_2$
Theoretical values: C: 58.55 H: 4.91 Cl: 19.20 Measured values: C: 58.39 H: 4.80 Cl: 19.48.

EXAMPLE 2

The reaction was conducted in the same manner as in Example 1 except that in Example 1, 9.93 g (50 mmol) of methyl α-chloro-β-phenylpropionate was used instead of α-chloro-β-phenylpropionitrile, whereby 8.9 g of crude crystals of α-chloro-β-phenylpropionic acid were obtained. (Yield: 96%)

EXAMPLE 3

The reaction was conducted in the same manner as in Example 1 except that in Example 1, 9.18 g (50 mmol) of α-chloro-β-phenylpropionic acid amide was used instead of α-chloro-β-phenylpropionitrile, whereby 9.0 g of crude crystals of α-chloro-β-phenylpropionic acid were obtained. (Yield: 98%)

EXAMPLE 4

The reaction was conducted in the same manner as in Example 1 except that in example 1, 10.50 g (50 mmol) of α-bromo-β-phenylpropionitrile was used instead of α-chloro-β-phenylpropionitrile. After the completion of the reaction, the organic phase and the aqueous phase were separated. To the organic phase, 50 ml of benzene was added, and then organic phase was washed twice with 30 ml of a saturated sodium chloride aqueous solution. The benzene phase was dried over anhydrous sodium sulfate, and then benzene was distilled off, whereby 10.2 g (yield: 89%) of α-bromo-β-phenylpropionic acid was obtained as oily substance.

Elemental analysis: As $C_9H_9BrO_2$
Theoretical values: C: 47.19 H: 3.96 Cl: 34.88
Measured values: C: 47.45 H: 3.78 Cl: 34.60

EXAMPLE 5

The reaction was conducted in the same manner as in Example 1 except that in Example 1, 35 ml of a 25 wt. % hydrochloric acid aqueous solution was used instead of 30 ml of concentrated hydrochloric acid, and the reaction time was changed to 3.5 hours, whereby 8.8 g (yield: 95%) of crude crystals of α-chloro-β-phenylpropionic acid were obtained.

EXAMPLE 6

The reaction was conducted in the same manner as in Example 1 except that in Example 1, a 70 wt. % sulfuric acid aqueous solution was used instead of 30 ml of concentrated hydrochloric acid, and the reaction time was changed to 5 hours, whereby 8.9 g (yield: 96%) of crude crystals of α-chloro-β-phenylpropionic acid was obtained.

EXAMPLE 7

The reaction was conducted in the same manner as in Example 1 except that in Example 1, the amount of the concentrated hydrochloric acid was changed to 15 ml, the reaction temperature was changed to 70° C. and the reaction time was changed to 5 hours, whereby 8.3 g (yield: 90%) of crude crystals of α-chloro-β-phenylpropionic acid were obtained.

We claim:

1. In a process for producing an α-halogeno-β-phenyl-propionic acid represented by the formula (I):

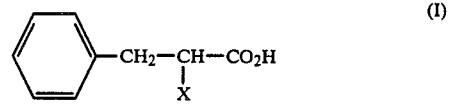

(I)

where X is a halogen atom, which comprises hydrolyzing under heating a halogen-containing ethylbenzene derivative represented by the formula (II):

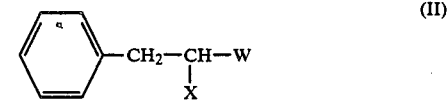

(II)

where W is a cyano group, an amidocarbonyl group or a lower alkoxycarbonyl group, and X is as defined above, and an aqueous mineral acid solution under vigorous stirring, the improvement which comprises conducting said reaction in a two-phase system in the absence of an organic acid.

2. The process according to claim 1, wherein the stirring is sufficiently vigorous to form and maintain an emulsion of the halogen-containing ethylbenzene derivative and the aqueous mineral acid solution during the hydrolysis.

3. The process according to claim 1, wherein the mineral acid in the aqueous mineral acid solution is hydrochloric acid, hydrobromic acid or sulfuric acid.

4. The process according to claim 1, wherein the amount of the mineral acid in the aqueous mineral acid solution is at least 3 mols relative to 1 mol of the halogencontaining ethylbenzene derivative.

5. The process according to claim 1, wherein the amount of the water in the aqueous mineral acid solution is at least two times the stoichiometric amount.

6. The process according to claim 1, wherein the concentration of the mineral acid in the aqueous mineral acid solution is at least about 15% by weight.

7. The process according to claim 1, wherein the reaction is conducted at a temperature of at least about 50° C.

* * * * *

UNITED STATES PATENT AND TRADEMARK OFFICE
CERTIFICATE OF CORRECTION

PATENT NO. : 4,594,450
DATED : June 10, 1986
INVENTOR(S) : Oyama, Kiyotaka et al.

It is certified that error appears in the above-identified patent and that said Letters Patent is hereby corrected as shown below:

-- The Priority information has been omitted on the Letters Patent. It should read as follows:

189858/1983  JAPAN  October 13, 1983. --

Signed and Sealed this

Second Day of September 1986

[SEAL]

Attest:

DONALD J. QUIGG

Attesting Officer

Commissioner of Patents and Trademarks